(12) United States Patent
Fuhrman et al.

(10) Patent No.: US 7,533,669 B2
(45) Date of Patent: May 19, 2009

(54) GAS DELIVERY SYSTEM AND METHOD (75) Inventors: Bradley P. Fuhrman, Buffalo, NY (US);
Mark S. Dowhy, West Seneca, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/833,509

(22) Filed: Aug. 3, 2007

(65) Prior Publication Data

US 2008/0029094 A1   Feb. 7, 2008

Related U.S. Application Data

(60) Provisional application No. 60/821,307, filed on Aug. 3, 2006.

(51) Int. Cl.
*A61M 11/00* (2006.01)

(52) U.S. Cl. ............................. 128/203.25; 128/203.24
(58) Field of Classification Search ............ 128/203.12, 128/203.25, 203.28, 204.23, 203.24
See application file for complete search history.

(56) References Cited

U.S. PATENT DOCUMENTS

| 6,230,708 B1 * | 5/2001 | Radko | 128/205.24 |
| 6,408,847 B1 * | 6/2002 | Nuckols et al. | 128/204.18 |
| 6,629,529 B2 * | 10/2003 | Arnott | 128/204.23 |

* cited by examiner

*Primary Examiner*—Steven O Douglas
(74) *Attorney, Agent, or Firm*—Hodgson Russ LLP (57) ABSTRACT

A gas delivery system and a method of delivering gas are disclosed. In one such system there is a housing and a displaceable partition. The housing may be divided by the partition into a respirator side and a patient side. The partition may have one or more holes extending through the partition to allow gas to move from one side of the partition to the other side of the partition.

20 Claims, 7 Drawing Sheets

GAS DELIVERY SYSTEM AND METHOD

CROSS-REFERENCE TO RELATED APPLICATION

This application claims the benefit of priority to U.S. provisional patent application Ser. No. 60/821,307, filed on Aug. 3, 2006.

FIELD OF THE INVENTION

The present invention relates to devices and methods of allowing for rebreathing of exhaled gases.

BACKGROUND OF THE INVENTION

Rebreathing circuits make it possible to reduce the amount of fresh gas delivered to a patient's lungs without raising blood carbon dioxide concentration. The reduction of fresh gas flow, in turn, conserves inhalational therapeutic agents. An example of this is the use of a rebreathing circuit to deliver volatile anesthesia. Other potential uses of rebreathing circuits include: efficient delivery of inhalational nitric oxide for pulmonary vasodilation, administration of helium gas as a means to reduce resistance to turbulent air flow in large airways, and reducing fresh gas flow as a means to limit evaporation of perfluorocarbon liquid from the lungs during partial liquid ventilation. Rebreathing circuits may also be used to enhance the delivery of aerosolized therapeutic agents for the delivery of drugs in particulate form to the lungs.

Rebreathing circuits are designed primarily to support anesthetic administration. In anesthesia applications, the gas in the rebreathing circuit is kept separate from the gas used to mechanically pressurize the respiratory circuit and thereby move the lungs. Were this separation to be incomplete or only partial, mixing of the gas streams might dilute the anesthetic being administered, which could result in the patient waking during surgery.

The prior art includes U.S. Pat. No. 4,989,597, which discloses a means to directly interface a ventilator to an anesthesia re-breathing circuit comprising a long, convoluted tube having a narrow diameter, yet large total volume. Such a device allows mixing of ventilator and re-breather gas streams. Under conditions of constant tidal volume, such a device causes a steady fractional admixture of the gas columns. Appropriate anesthetic concentration in the re-breather is maintained by delivery of an excess of anesthetic to the re-breather as compensation for losses due to mixing with the ventilator gas column. In that system, there is no divider between the separated gas columns. Instead there is an "open separation" of the gases resulting from the long mixing tube, which may contain two to three liters of gas.

SUMMARY OF THE INVENTION

The invention may be embodied as a gas delivery system that has a housing and a displaceable partition. The housing may be divided by the partition into a respirator side and a patient side. The partition may have a first side and a second side, the first side facing the patient side of the housing, and the second side facing the respirator side of the housing. A respirator may be connected to the respirator side of the housing so that the respirator is able to move the partition.

In one embodiment of the invention, the respirator is omitted, and breathing by the patient is relied on to move the partition. In that embodiment, the respirator side of the housing may be connected to an oxygen source or a source of fresh air, or to a ventilator.

The partition may have one or more holes extending through the partition to allow some gas to move from one side of the partition to the other side of the partition. In this manner, the partition limits but does not prevent gas from flowing from one side of the partition to the other side of the partition. The one or more holes collectively may have an area of about ¼ $cm^2$.

The invention may be embodied as a method. In one such method, a gas delivery system is provided. For example, the gas delivery system may be the system described above. The partition may be caused to move so as to cause some gas to flow through the holes of the partition. For example, the respirator may be operated so that the partition is caused to move. Operation of the respirator may be accomplished so as to cause some gas to pass from the respirator side of the housing to the patient side of the housing via the holes in the partition. Operation of the respirator may be accomplished so as to cause some gas to pass from the patient side of the housing to the respirator side of the housing via the holes in the partition. In another embodiment, the partition is caused to move by a patient breathing into the housing.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF THE INVENTION

The invention may be embodied as a gas delivery system having a displaceable partition. The gas delivery system may be used to deliver respiratory gases to and from a patient. For example, the gases delivered to a patient may include oxygen necessary to sustain the life of the patient. The gases delivered to a patient may also include therapeutic drugs, such as those designed to treat unwanted conditions in the patient. One such drug is levalbuterol aerosol.

Figure 1:
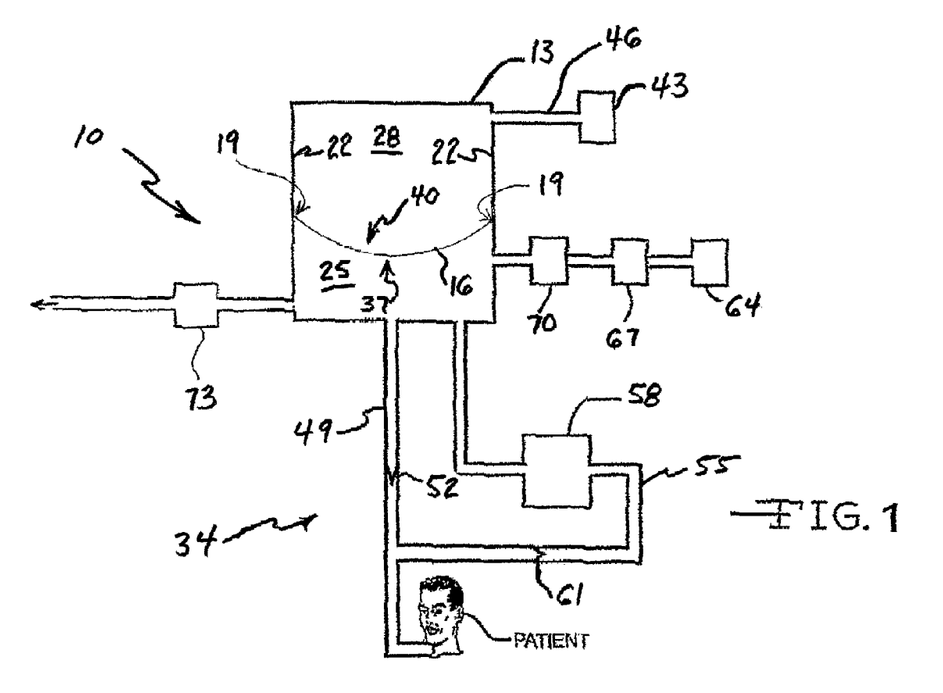
FIG. 1 is a schematic representation of a system according to the invention.
Figure 2:
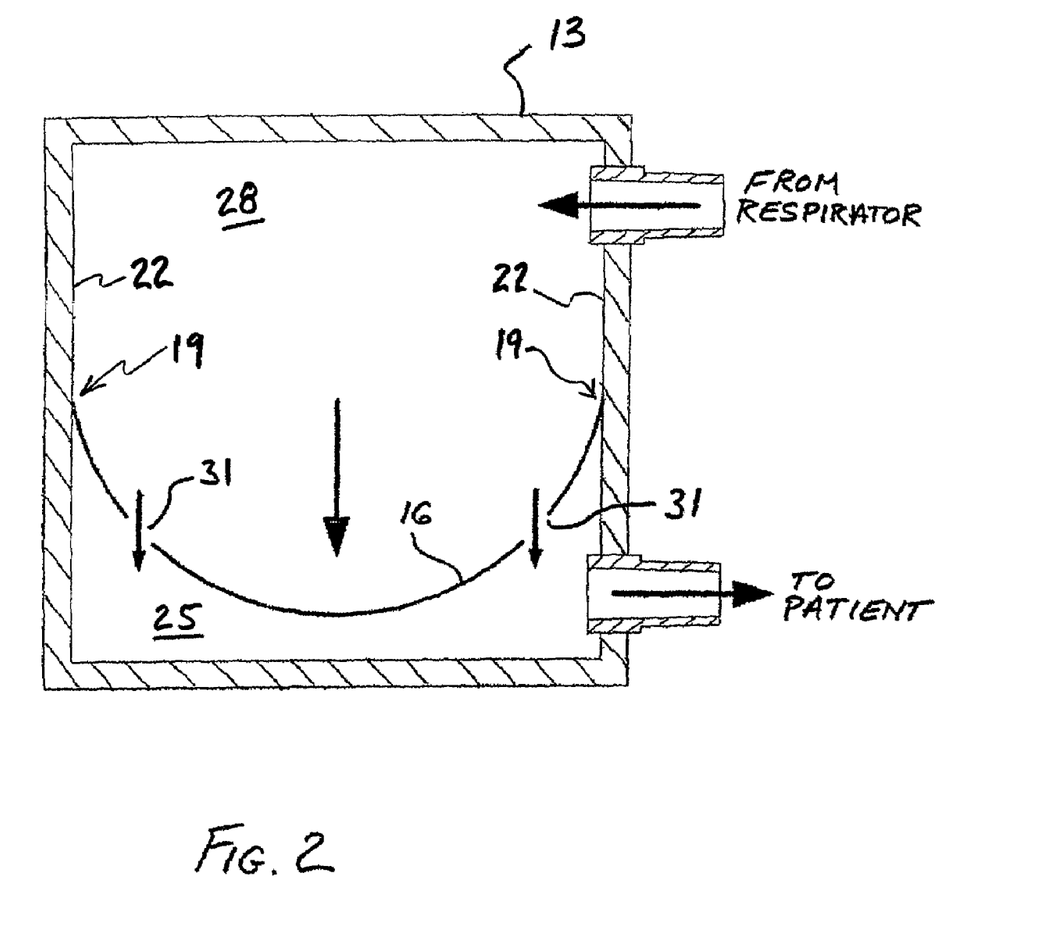
FIG. 2 depicts a housing and a displaceable partition according to the invention.
Figure 3:
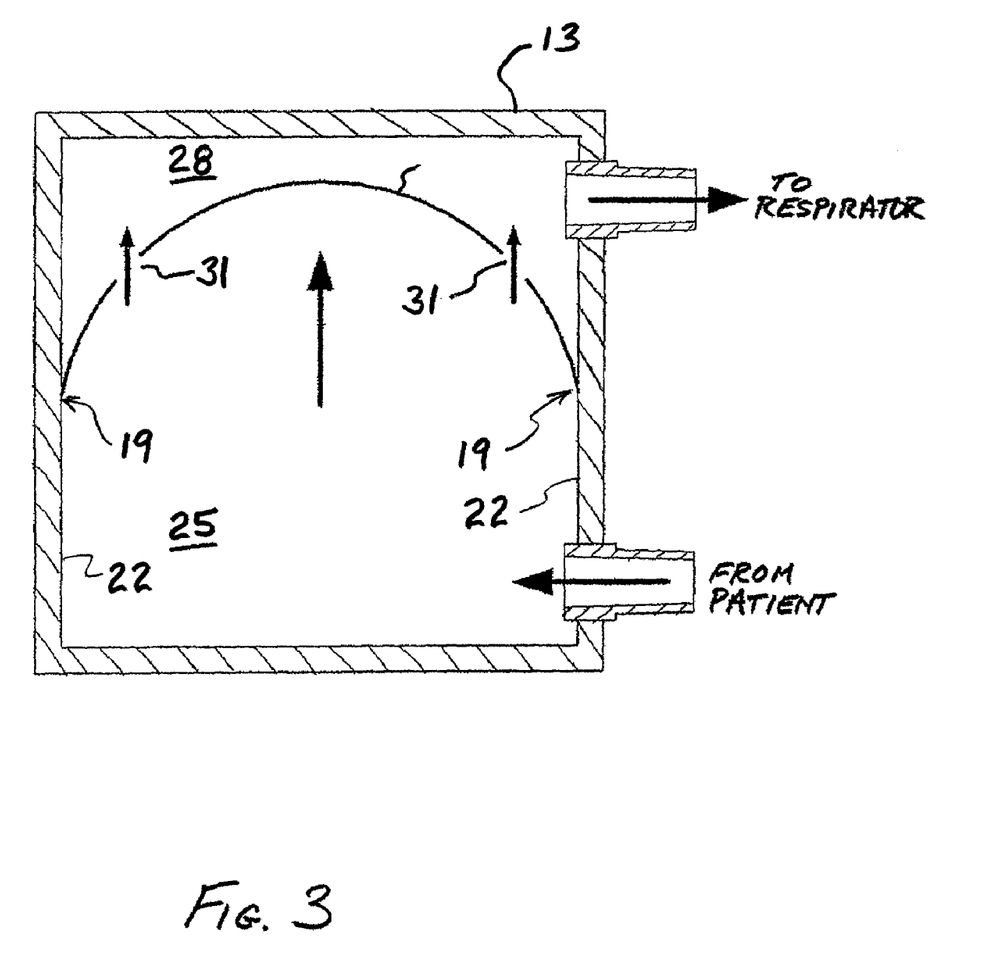
FIG. 3 is similar to FIG. 2, except that the direction of gas flow and the position of the partition has changed.
Figure 4:
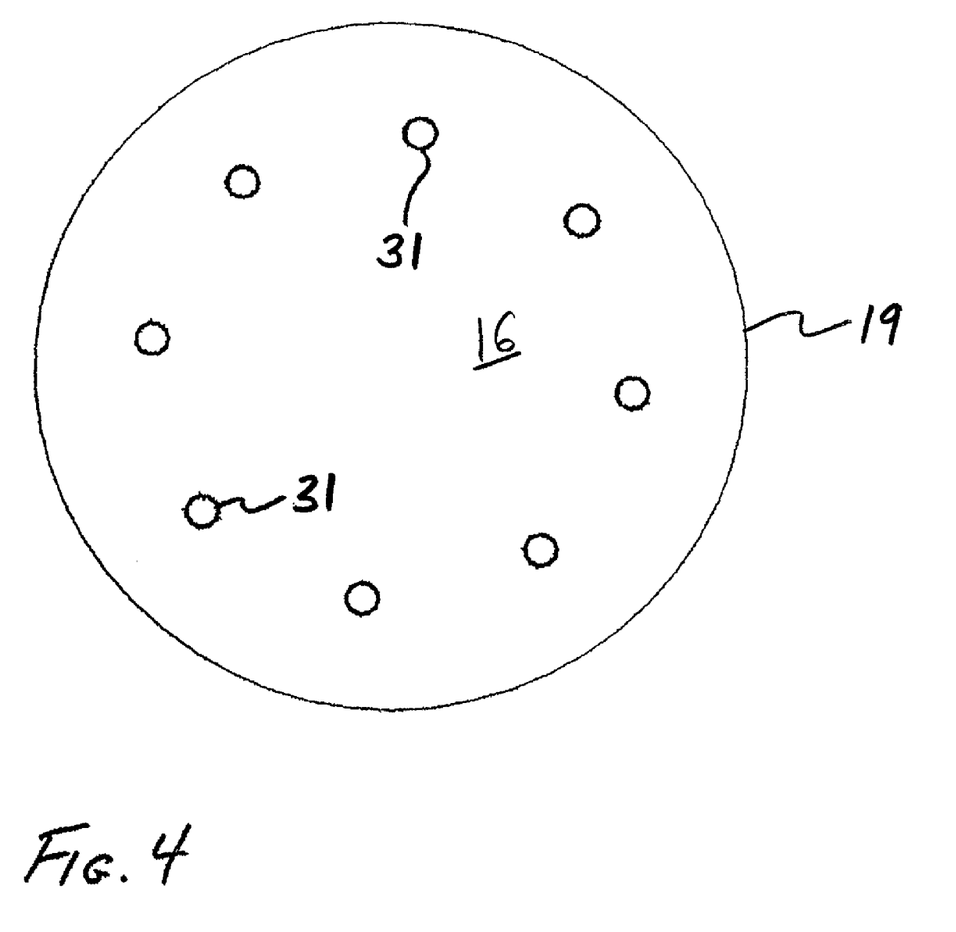
FIG. 4 depicts a partition according to the invention.

FIG. 1 depicts a gas delivery system 10 that is in keeping with the invention. In FIG. 1, there is a housing 13 and a displaceable partition 16. A perimeter edge 19 of the partition 16 is shown sealed to an interior surface 22 the housing 13. The partition 16 divides the housing 13 into two chambers. One of the chambers 25 is referred to herein as the "patient side" and the other chamber 28 is referred to herein as the "respirator side". The partition 16 has one or more holes 31 extending through the partition 16 so as to allow some gas to move from one side of the partition 16 to the other side of the partition 16. FIGS. 2 through 4 show holes 31 in the partition 16. As such, the partition 16 partially separates the gas on the patient side 25 of the housing 13 from the gas on the respirator side 28 of the housing 13.

Because the invention is not intended for the delivery of anesthetic gases, a small amount of mixing between patient side 25 gas and the respirator side 28 gas is not deleterious. Unexpected awakening is not an anticipated complication of "partial separation" of gases in this setting. Moreover, a small amount of mixing may be used to provide sufficient fresh gas (including oxygen) to a re-breathing device 34 in order to eliminate the need for a distinct inflow of fresh gas. Such a re-breathing device 34 may have one side connected to the patient side 25 of the housing 13, and another side connected to a patient, and thereby allow gas from the patient side 25 to flow toward a patient during inhalation, and toward the housing 13 during exhalation.

A re-breathing device may be as simple as a gas-communication line, which conveys gas from the patient side 25 of the housing 13 toward a patient during inhalation, and also conveys gas from the patient toward the patient side 25 of the housing 13 during exhalation. More sophisticated re-breathing devices are possible. For example, the re-breathing device may be a compliant bag, or a circle-circuit. FIG. 1 shows a re-breathing device 34 that is a circle circuit.

The displaceable partition 16 may be made from a flexible material, such as rubber, silastic, silicone, plastic or other light weight material. The displaceable partition 16 may have a first side 37 that faces the patient side 25 and a second side 40 that faces the respirator side 28. A respirator 43 forces gas into and out of the housing 13, in order to cause the displaceable partition 16 to move. The respirator 43 may be connected to the housing 13 via a gas-communication line 46 having a first end connected to the respirator side 28 of the housing 13, and a second end connected to the respirator 43.

In the embodiment depicted in FIG. 1, when the respirator 43 forces gas into the respirator side 28, the displaceable partition 16 forces gas toward the patient via a gas-communication line 49. FIG. 1 and FIG. 2 show a position of the partition 16 when the respirator 43 is forcing gas into the respirator side 28.

The gas-communication line 49 may be provided to have a first end connected to the patient side 25 of the housing 13, and a second end connected to a patient, in order to convey gas toward the patient. A check valve 52 in the gas-communication line 49 may be included so that the flow of gas is substantially uni-directional through the gas-communication line 49. When the check valve 52 is open, gas is permitted to move through the gas-communication line 49, and when the check valve 52 is closed, gas is prevented from moving through the gas-communication line 49. In this manner, when the check valve 52 is open, gas on the patient side 25 of the housing 13 is permitted to leave the housing 13.

FIG. 1 also shows a gas-communication line 55 having a first end connected to the patient side 25 of the housing 13. A carbon-dioxide scrubber 58 may be included in the gas-communication line 55. A check valve 61 may be positioned to allow gas to move through the gas-communication line 55 when the check valve 61 is open, and to prevent gas from moving through the gas-communication line 55 when the check valve 61 is closed. As such, when the check valve 61 is open, gas in the gas-communication line 55 is allowed to enter the patient side 25. For example, when the patient exhales or the respirator 43 forces gas out of the housing 13, gas is delivered from the patient to the gas-communication line 55. In this manner, the gas-communication line 55 delivers gas back to the patient side 25 of the housing 13. The exhaled gas from the patient may be caused to pass through the $CO_2$ scrubber 58.

An inspiratory gas source 64 may provide fresh gas, which may include enough oxygen to replace that consumed by the patient. A controller 67 may be used to allow a desired amount of fresh gas to enter the housing 13.

A therapeutic agent delivery system 70, such as a nebulizer or vaporizer, may provide a therapeutic agent in the form of fine particles, gas or vapor. In FIG. 1, the therapeutic agent delivery system 70 is shown in a position to deliver a therapeutic agent to the patient side 25 of the housing 13. It should be noted that in alternate embodiments of the system 10, the gas source 64 and/or the therapeutic agent delivery system 70 may be located elsewhere, for example in the rebreathing device 34.

It may be necessary to assure that the pressure on the patient side 25 does not exceed a desired level. A valve 73 may be provided to assure the patient side 25 does not exceed a desired pressure. If the pressure on the patient side 25 reaches a threshold level, which is too high, the valve 73 may open to allow gas to be released from the patient side 25.

FIGS. 2 and 3 are cross-sectional views showing the housing 13 and the partition 16. The arrows in FIGS. 2 and 3 indicate the direction of gas flow. In FIG. 2, the respirator 43 is forcing gas toward the patient. In FIG. 3, gas is flowing away from the patient. It will be noted that the partition 16 allows some gas to move through the partition 16 via the holes 31.

FIG. 4 depicts a partition 16 having eight holes 31, two of which are identified. The holes 31 allow some gas to move from one side of the partition 16 to the other side of the partition 16. For a system used with a human being, it is believed that the total amount of hole-area may be about one-quarter of a square centimeter. In such a system, the partition 16 may have a diameter of up to 10 inches. Therefore, for a partition having eight holes 31, the average hole 31 size may be about $\frac{1}{32}^{nd}$ $cm^2$.

Figure 5:
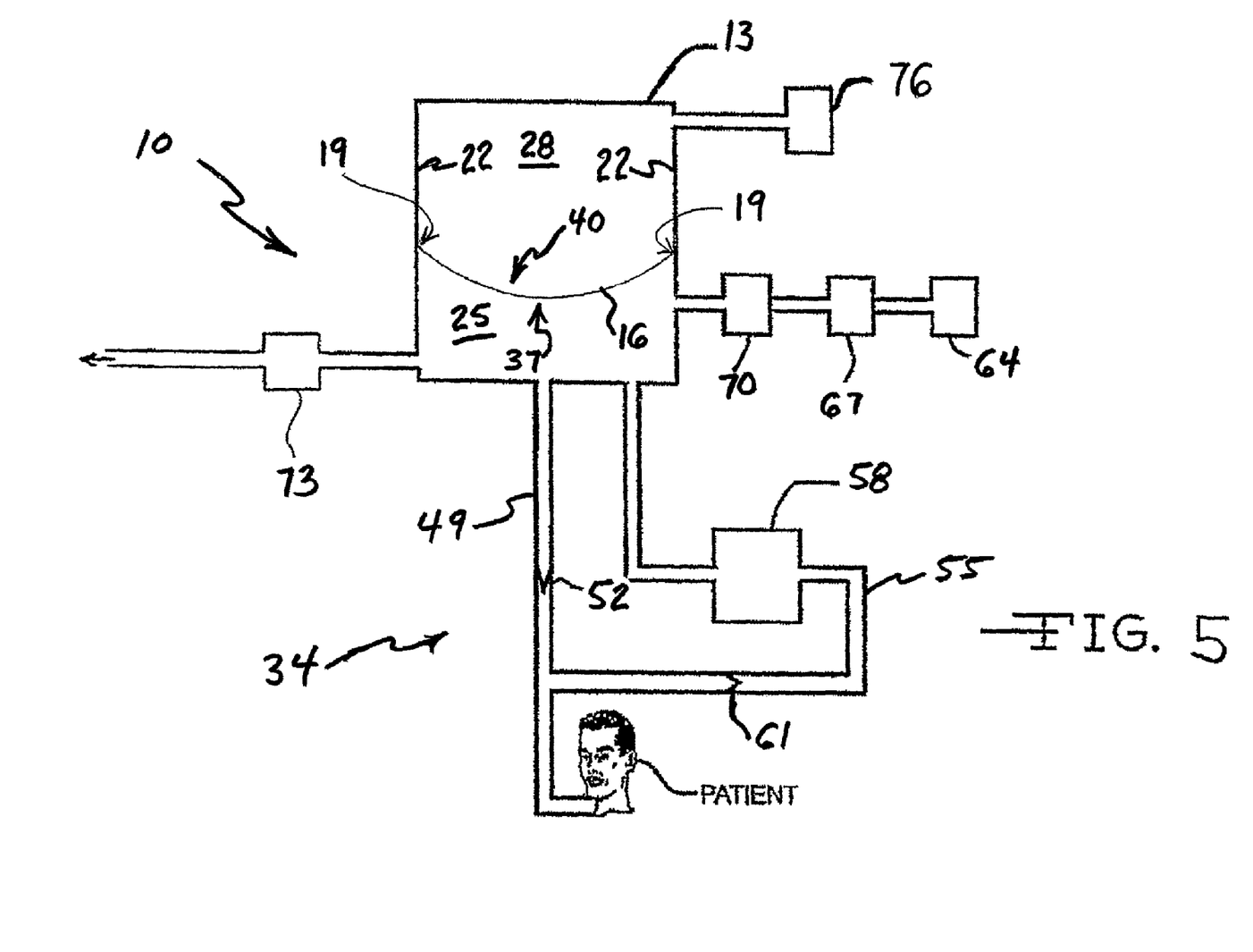
FIG. 5 is a schematic representation of a system according to the invention that does not include a respirator.

FIG. 5 depicts a gas delivery system 10 that is in keeping with the invention. Unlike the system depicted in FIG. 1, in FIG. 5 there is no respirator. In the embodiment of FIG. 5, the patient's breathing moves the partition. The respirator side 28 of the housing may be connected to an oxygen source or a fresh gas source, or to a ventilator. In FIG. 5, the respirator side 28 is shown connected to a source of fresh gas 76. The embodiment of FIG. 5 should allow for conservation of a therapeutic agent by encouraging rebreathing of the therapeutic agent introduced by the therapeutic agent delivery system 70, but possibly not to the same degree as the embodiment depicted in FIG. 1.

Figure 6:
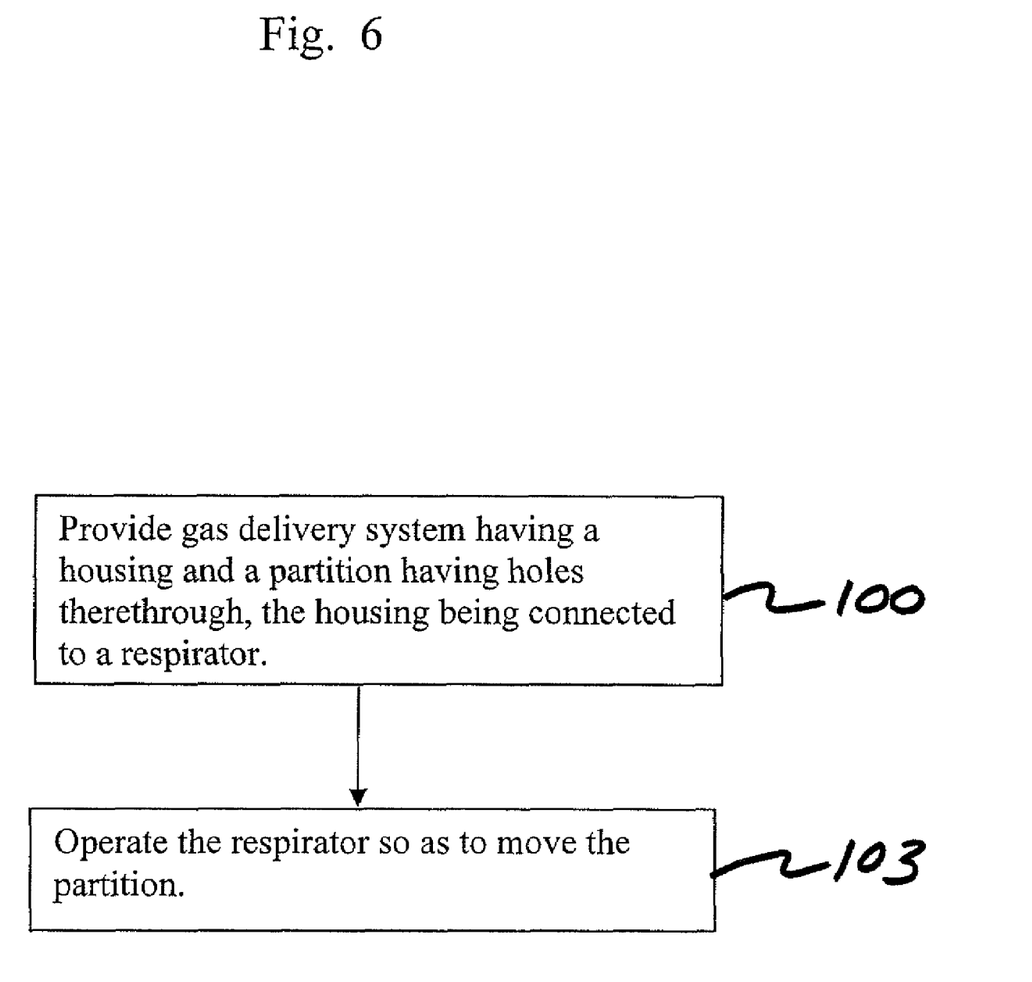
FIG. 6 is a flow chart depicting a method according to the invention.

The invention may be embodied as a method. One such method is depicted in FIG. 6. In that method, a gas delivery system, such as those described above, is provided 100. The respirator is then operated 103 so as to cause the partition to move. For example, the respirator may be operated 103 to force gas into the respirator side of the housing, and thereby cause gas to pass from the respirator side to the patient side via the holes in the partition. Doing so, may have the effect of causing gas from the respirator to enter the respirator side.

The respirator may also be operated 103 so as to remove gas from the respirator side, and thereby cause gas to pass from the patient side to the respirator side via the holes. Doing so may also have the effect of causing some gas from the patient to enter the patient side.

Figure 7:
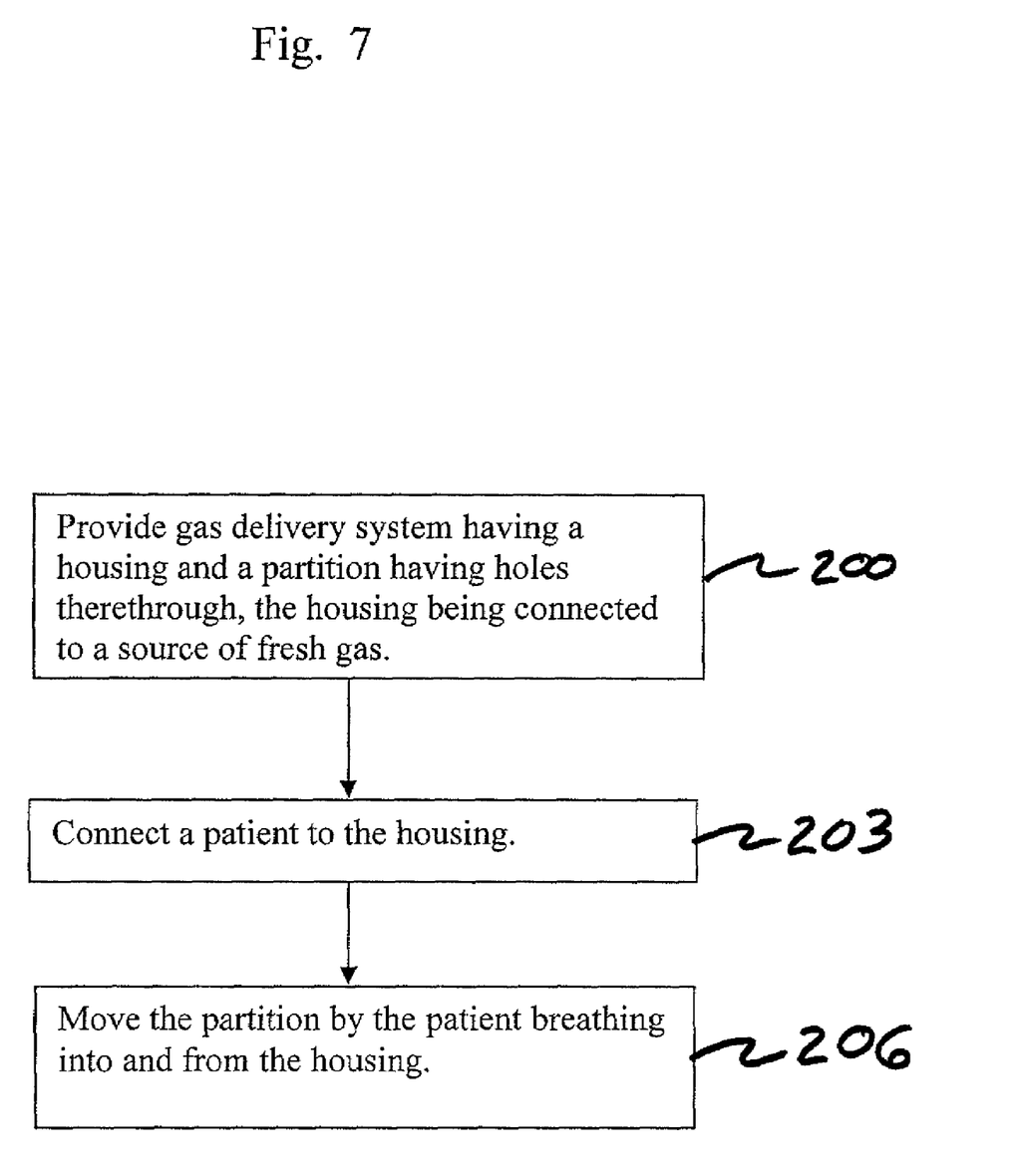
FIG. 7 is a flow chart depicting another method according to the invention.

Another method according to the invention is depicted in FIG. 7. In that method, a gas delivery system, such as those described above, is provided 200, but in lieu of a respirator, a fresh gas source is connected to the respirator side of the housing. A patient is connected 203 to the housing, and allowed to breath into and from the housing. As the patient inhales from the housing and exhales into the housing, the partition is caused 206 to move. During inhalation, some gas is caused to pass from the respirator side to the patient side via the holes in the partition. Doing so, may have the effect of causing gas from the fresh gas source to enter the respirator side.

Further with regard to FIG. 7, during exhalation, gas is caused to pass from the patient side to the respirator side via the holes. Doing so may also have the effect of causing some gas from the patient to enter the patient side.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A gas delivery system, comprising:
   a housing having a respirator side and a patient side;
   a displaceable partition having a first side and a second side, the first side facing the patient side of the housing, and the second side facing the respirator side of the housing, the partition having one or more holes extending through the partition to allow some gas to move from the first side of the partition to the second side of the partition when a pressure on the patient side exceeds a pressure on the respirator side and from the second side of the partition to the first side of the partition when a pressure on the respirator side exceeds a pressure on the patient side; and
   a respirator connected to the respirator side of the housing so as to be able to move the partition.

2. The gas delivery system of claim 1, wherein the partition is made from a flexible, material.

3. The gas delivery system of claim 1, wherein a perimeter edge of the partition is sealed with an interior surface of the housing to prevent gas from passing between the edge and the housing.

4. The gas delivery system of claim 1, wherein the one or more holes collectively have an area of about $\frac{1}{4}$ cm$^2$.

5. The gas delivery system of claim 1, further comprising a gas-communication line having a first end connected to the respirator side of the housing, and a second end connected to the respirator.

6. The gas delivery system of claim 1, further comprising a gas-communication line having a first end connected to the patient side of the housing, and a second end connected to a patient.

7. The gas delivery system of claim 6, further comprising a check valve positioned to allow gas to move through the gas-communication line when the check valve is open, and to prevent gas from moving through the gas-communication line when the check valve is closed.

8. The gas delivery system of claim 7, wherein when the check valve is open, gas on the patient side of the housing leaves the housing.

9. The gas delivery system of claim 1, further comprising a gas-communication line having a first end connected to the patient side of the housing, and the gas-communication line includes a carbon-dioxide scrubber.

10. The gas delivery system of claim 9, further comprising a check valve positioned to allow gas to move through the gas-communication line when the check valve is open, and to prevent gas from moving through the gas-communication line when the check valve is closed.

11. The gas delivery system of claim 10, wherein when the check valve is open, gas in the gas-communication line enters the patient side.

12. A method of delivering gas, comprising:
    providing a system having (a) a housing, the housing including a respirator side and a patient side, and (b) a displacable partition, the partition including a first side and a second side, the first side facing the respirator side of the housing, and the second side facing the patient side of the housing, the partition having one or more holes extending through the partition to allow some gas to move from the first side of the partition to the second side of the partition when a pressure on the patient side exceeds a pressure on the respirator side and from the second side of the partition to the first side of the partition when a pressure on the respirator side exceeds a pressure on the patient side;
    moving the partition so as to cause some gas to flow through the holes.

13. The method of claim 12, wherein the respirator is operated so as to cause some gas to pass from the respirator side to the patient side via the holes.

14. The method of claim 13, wherein operation of the respirator also causes gas from the respirator to enter the respirator side.

15. The method of claim 12, wherein the respirator is operated so as to cause some gas to pass from the patient side to the respirator side via the holes.

16. The method of claim 15, wherein operation of the respirator also causes gas from a patient to enter the patient side.

17. A gas delivery system, comprising:
    a housing having a respirator side and a patient side;
    a displaceable partition having a first side and a second side, the first side facing the patient side of the housing, and the second side facing the respirator side of the housing, the partition having one or more holes extending through the partition to allow some gas to move from the first side of the partition to the second side of the partition when a pressure on the patient side exceeds a pressure on the respirator side and from the second side of the partition to the first side of the partition when a pressure on the respirator side exceeds a pressure on the patient side; and
    a source of fresh gas connected to the respirator side of the housing.

18. The gas delivery system of claim 17, wherein the one or more holes collectively have an area of about $\frac{1}{4}$ cm$^2$.

19. The gas delivery system of claim 18, further comprising a gas-communication line having a first end connected to the patient side of the housing, and a second end connected to a patient.

20. The gas delivery system of claim 18, further comprising a gas-communication line having a first end connected to the patient side of the housing, and the gas-communication line includes a carbon-dioxide scrubber.

* * * * *